United States Patent [19]

Fain et al.

[11] Patent Number: 5,649,971
[45] Date of Patent: Jul. 22, 1997

[54] APPARATUS AND METHOD FOR INDUCING FIBRILLATION

[75] Inventors: Eric S. Fain, Menlo Park; Benjamin D. Pless, Atherton, both of Calif.

[73] Assignee: Ventritex, Inc., Sunnyvale, Calif.

[21] Appl. No.: 568,044

[22] Filed: Dec. 6, 1995

[51] Int. Cl.⁶ .................................................. A61N 1/362
[52] U.S. Cl. ............................................. 607/72; 607/2
[58] Field of Search ............................. 607/4, 5, 8, 72, 607/74, 75

[56] References Cited

U.S. PATENT DOCUMENTS

| | | | |
|---|---|---|---|
| 3,602,229 | 8/1971 | Jaros | 607/72 |
| 5,129,392 | 7/1992 | Bardy et al. | |
| 5,215,083 | 6/1993 | Drane et al. | |
| 5,279,293 | 1/1994 | Andersen et al. | 607/5 |
| 5,395,373 | 3/1995 | Ayers | 607/8 |
| 5,470,341 | 11/1995 | Kuehn et al. | 607/5 |
| 5,489,293 | 2/1996 | Pless et al. | 607/5 |

FOREIGN PATENT DOCUMENTS 589252  3/1994  European Pat. Off. ............... 607/5

OTHER PUBLICATIONS

"Digital System for Artificial Fibrillation of Animal Hearts", Schwingshacki, et al., *Biomedical Engineering*, vol. 8, No. 11, Nov. 1973, pp. 472–474.

"Cadence® Tiered therapy Defibrillator System—V–100 Serial Pulse Generator and Programmer", Physician's Manual, Ventritex, Inc., Jan. 1993.

*Primary Examiner*—Jeffrey R. Jastrzab
*Attorney, Agent, or Firm*—Steven M. Mitchell; Mark J. Meltzer

[57] ABSTRACT

A method and apparatus for inducing fibrillation in a patient's heart by delivering a direct current stimulus to the heart from a DC-to-DC converter. The hardware of a conventional implantable cardioverter/defibrillator (ICD) is utilized with a modification to the control algorithms. Particularly, when it is desired to induce fibrillation in a patient's heart, typically during ICD implant defibrillation threshold (DFT) testing, a command is delivered from an external instrument to the ICD to deliver the fibrillation shock. The DC-to-DC converter which is normally used to charge the ICD high voltage capacitors is activated and immediately thereafter or following a short period to allow the high voltage capacitors to charge, the high voltage output switches of the output stage are closed. This delivers the output current from the DC-to-DC converter to the defibrillation electrodes and through the patient's heart. This stimulus is continued for a predetermined time of between about 30 milliseconds to 5 seconds. At that point the output switches are opened and the converter is shut off. This DC stimulus delivered directly to the patient's heart induces fibrillation.

24 Claims, 2 Drawing Sheets

APPARATUS AND METHOD FOR INDUCING FIBRILLATION

BACKGROUND OF THE INVENTION

1. Field of the Invention

The present invention relates generally to medical stimulators and more specifically to implantable cardioverters and defibrillators.

2. Description of the Prior Art

When implanting an implantable defibrillator, it is desirable to test the device's operability to ensure that it is capable of reliably defibrillating the heart. In order to accomplish this, it is necessary to first induce fibrillation in the patient's heart, and then determine whether the implantable defibrillator is capable of terminating the induced fibrillation. Typically, rapid pacing from the implanted defibrillator or an external pulse generator or an external 60 Hz low voltage transformer has been used in inducing fibrillation.

It would be desirable to improve the fibrillation induction function in an implantable defibrillator, to allow for a more fully automated testing regimen and to simplify the implantation procedure. However, incorporation of a 60 Hz fibrillator into an implantable device poses substantial technical difficulties. In any case, rapid pacing and 60 Hz fibrillators frequently fail to induce fibrillation.

U.S. Pat. No. 5,129,392 to Bardy et al discloses an automatic fibrillator for inclusion in an implantable defibrillator. Fibrillation is induced using overdrive pacing. The effective refractory period of the patient's heart is measured during pacing. A fibrillation inducing pulse is delivered at a calculated time interval following an overdrive pacing pulse. This approach requires complex timing calculations and may not be effective in all cases in inducing fibrillation.

U.S. Pat. No. 5,215,083 to Drane et al discloses an apparatus and method for fibrillation induction. At least a portion of a pulse train of "micro-shocks" delivered from the high voltage capacitors are synchronized to the patient's T-waves. The length of the series of trains and the micro-shock pulse widths are programmable parameters and the polarity of the shocks may be alternated within a train. This technique is also complex and may not be consistently effective.

It is therefore an object of the invention to provide a method and apparatus for inducing fibrillation in a patient's heart.

SUMMARY OF THE INVENTION

The present invention provides a method and apparatus for inducing fibrillation in a patient's heart by delivering a direct current (DC) stimulus to the heart. In a preferred embodiment of the invention, the hardware of a conventional implantable cardioverter/defibrillator (ICD) is utilized with a modification to the control algorithms. Particularly, when it is desired to induce fibrillation in a patient's heart, typically during ICD implant defibrillation threshold (DFT) testing, a command is delivered from an external instrument to the ICD to deliver the DC stimulus to induce fibrillation. The DC stimulus may be either R-wave synchronous or asynchronous. The DC stimulus is provided from either the ICD battery or DC-to-DC converter. To initiate a stimulus using the DC-to-DC converter, which comprises a step-up transformer normally used to charge the ICD high voltage capacitors, the converter is activated. Immediately thereafter or following a short period to allow the high voltage capacitors to charge or to synchronize with an R-wave, the high voltage output switches of the ICD output stage are closed. This delivers the output current from the DC-to-DC converter to the defibrillation electrodes and through the patient's heart. To deliver the DC stimulus from the battery, the switches connecting the battery to the converter and the output switches are closed thus connecting the battery to the defibrillation electrodes. The defibrillation electrodes are those known in the art, preferably transvenous lead defibrillation electrodes or epicardial patch electrodes. The DC stimulus is continued for a predetermined time of between about 30 milliseconds to 5 seconds. At that point the output switches are opened and the converter is shut off. This DC stimulus delivered directly to the patient's heart induces fibrillation. Fibrillation induction is of course followed by the ICD detecting the fibrillation and delivering a programmed defibrillation shock to rescue the patient.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
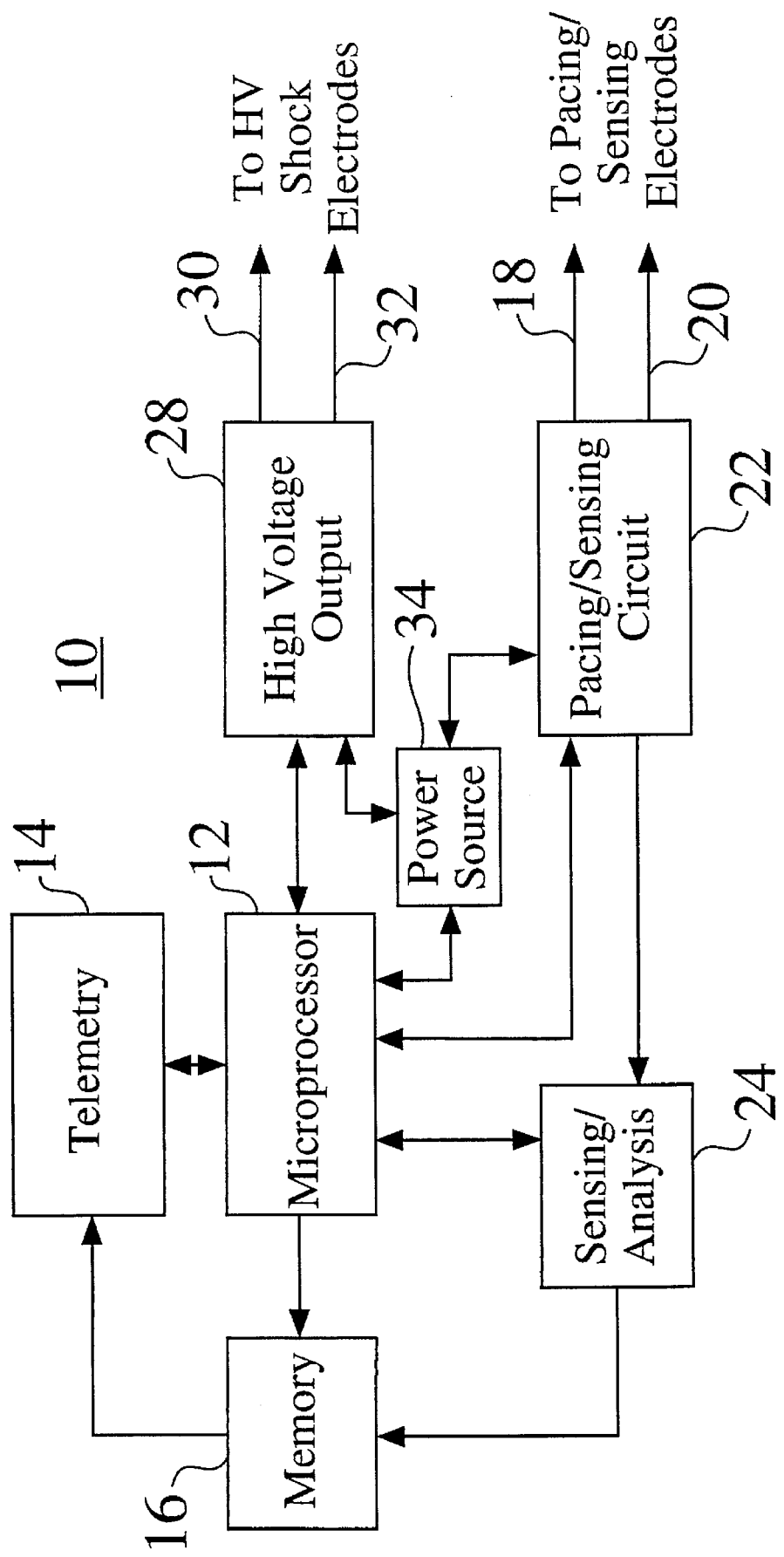
FIG. 1 is a block diagram of an implantable cardioverter/defibrillator according the invention.

The invention will now be discussed with reference to FIG. 1 which is a block diagram of an implantable cardioverter/defibrillator (ICD) 10. The method of the invention can be practiced with the currently designed ICDs such as the one described in U.S. Pat. No. 5,111,816 to Pless et al., which patent is incorporated herein by reference. The apparatus of the invention simply requires modification of the control algorithms of the ICD.

ICD 10 includes a microprocessor 12 which controls the primary functions of the ICD. Control could alternatively be achieved with a state machine. The microprocessor 12 communicates with an external programmer (not shown) through a telemetry section 14. Commands from the programmer through telemetry section 14 to microprocessor 12 are used to send commands to the ICD including fibrillation induction. Telemetry section 14 can also be used to transmit stored electrograms and other device information from a memory section 16 to the programmer, as is well known in the art.

Sensing of electrograms from a patient's heart is achieved through a pair of sensing conductors 18, 20 coupled on one end to sensing electrodes (not shown) proximate the patient's heart and on the other end to a pacing/sensing circuit 22. Sensed electrograms are provided to a sensing/analysis circuit 24 which communicates with and is controlled by microprocessor 12.

In a preferred embodiment of the invention, ICD 10 can provide a number of different therapies to the patient's heart in response to detected arrhythmias including bradycardia pacing, antitachycardia pacing, cardioversion and defibrillation shocks. Pacing is provided under control of microprocessor 12 by a pacing/sensing circuit 22 and conductors 18, 20. High voltage cardioversion and defibrillation shocks are provided under control of microprocessor 12 by high voltage output circuit 28 which will be discussed in more detail with reference to FIG. 2 below. The high voltage shocks are provided between a pair of terminals coupled to conductors 30, 32. These conductors are coupled to at least a pair of high voltage electrodes (not shown). There are numerous pacing/sensing electrode and high voltage electrode configurations known in the art, any of which could be used in practice of the present invention. These include bipolar, integrated bipolar and unipolar sensing configurations and high voltage electrodes including a fight ventricular defibrillation electrode, superior vena cava defibrillation electrode, a subcutaneous patch electrode, a defibrillator can electrode and others.

ICD 10 further includes a power source 34 which provides power to the various circuits of the device. The power source is one or more low voltage, high current batteries, for example a lithium silver vanadium oxide battery.

Figure 2:
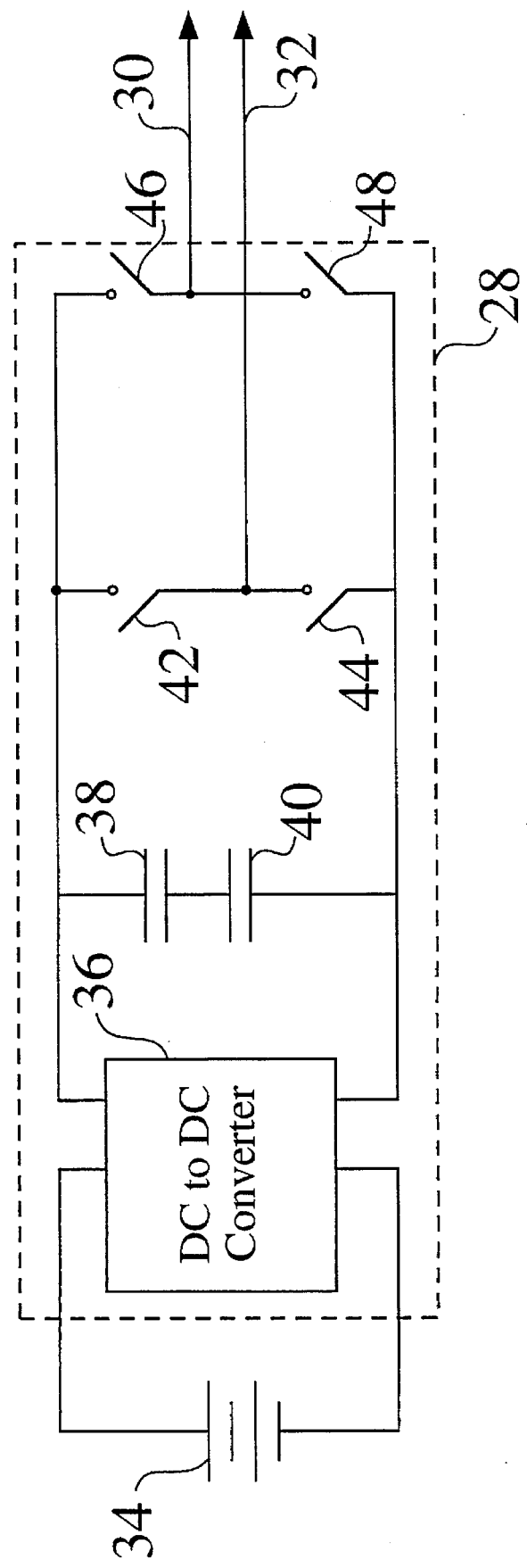
FIG. 2 is a schematic diagram of the high voltage output stage of the invention.

Referring now to FIG. 2, the power source 34 and high voltage output circuit 28 of ICD 10 are shown. Battery 34 is coupled to a DC-to-DC converter 36 of the type well known in the art. Such a DC-to-DC converter is disclosed in U.S. Pat. Nos. 4,257,087 and 4,186,437 to Cuk which patents are hereby incorporated by reference. The principal component of DC-to-DC converter 36 is a step-up flyback transformer which is used to charge a pair of series connected high voltage capacitors 38, 40. One or more capacitors could be used but two series connected aluminum electrolytic capacitors are typically used.

Output circuit 28 further includes an H-bridge circuit including switches 42, 44, 46 and 48 which are under control of microprocessor 12. The H-bridge circuit is provided to allow the delivery of biphasic cardioversion and defibrillation shocks to the patient's heart. Only two switches are required to practice the invention. However, with the H-bridge circuit shown in FIG. 2, the pulse from DC-to-DC converter 36 can be provided to the patient's heart in either polarity by selectively closing switches 42 and 48 together or switches 44 and 46 together. It has been found that having the electrode in the right ventricle positive provides better results. Other known output switching configurations could be used.

In an alternative embodiment of the invention, the DC stimulus is provided directly from the battery 34. Switches within DC-to-DC converter couple the battery to the output stage without activating the transformer. Alternatively, the battery can be coupled to the patient's heart through pacing/ sensing circuit 22 and conductors 18, 20 to the pacing/ sensing electrodes (not shown).

The method of the invention will now be described. The invention is typically used at the time an ICD is being implanted to assist in performing defibrillation threshold (DFT) testing. In this procedure, a stimulus is delivered to the patient's heart to induce fibrillation and the ICD being implanted is allowed to detect the fibrillation and deliver a defibrillation shock. Using the ICD to provide the fibrillation inducing stimulus as well as the defibrillation shock simplifies the DFT testing procedure. It is also useful for follow-up testing to avoid surgery to place an additional catheter for fibrillation induction. When the implanting physician is ready to induce fibrillation, a command is sent from the external programmer (not shown) through telemetry section 14 to microprocessor 12. The DC stimulus from DC-to-DC converter 36 can be delivered either synchronous with a sensed R-wave or asynchronously. If the DC stimulus is to be delivered synchronously, stimulus delivery is delayed until the next sensed R-wave.

Microprocessor 12 issues several commands to deliver the DC stimulus. The DC-to-DC converter 36 is actuated by repetitively coupling battery 34 to the transformer coil in the converter. A pair of switches in high voltage output circuit 28 are then closed directly coupling the output of DC-to-DC converter 36 to the patient's heart through conductors 30, 32 and the defibrillation electrodes. The switches remain closed and the DC-to-DC converter 36 is actuated for a period between about 0.03 to 5 seconds. This period is more preferably between about 0.3 and 3 seconds. The period may be programmed by the physician using the external programmer. As discussed above, either switch pair 42, 48 or 44, 46 may be used to deliver the fibrillation inducing stimulus.

In an alternative embodiment, the voltage level of the DC stimulus is regulated by sensing the output of the DC-to-DC converter and modulating the pulse width or frequency of the DC-to-DC converter.

It should be understood that various alternatives to the embodiments of the invention described herein may be employed in practicing the invention. For example, a DC-to-DC converter in an external instrument could be used for fibrillation induction. It is thus intended that the following claims define the scope of the invention and that structures and methods within the scope of these claims and their equivalents be covered thereby.

What is claimed is:

1. A method of inducing fibrillation in a patient's heart using an implantable pulse generator, comprising:

activating in said pulse generator a DC-to-DC converter having an output which can be coupled to electrodes positioned in or near said patient's heart; and coupling the output of said DC-to-DC converter to said electrodes to deliver a fibrillation inducing stimulus.

2. The method of claim 1 wherein said coupling step includes closing a pair of output switches in a defibrillation output stage of said implantable pulse generator.

3. The method of claim 2 and further including the step of coupling the output of said DC-to-DC converter to a high voltage capacitor means coupled in parallel with said output switches for a predetermined time prior to closing said output switches.

4. The method of claim 1 wherein said coupling step includes closing a pair of output switches in a pacing output stage of said implantable pulse generator.

5. The method of claim 1 and further including the step of disconnecting the output of said DC-to-DC converter from said patient's heart following a time period of between 0.03 and 5 seconds.

6. The method of claim 5 wherein said step of disconnecting comprises opening a pair of output switches in a defibrillation output stage of said implantable pulse generator.

7. The method of claim 1 and further including the step of deactivating said DC-to-DC converter following a time period of between 0.03 and 5 seconds.

8. The method of claim 1 and further including the step of sensing an electrogram signal from said patient's heart and delivering said fibrillation inducing stimulus to said patient's heart synchronous with a sensed R wave.

9. The method of claim 1 and further including the step of delivering a command from an external control device to initiate delivery of said fibrillation inducing stimulus.

10. An automatic fibrillator for inducing fibrillation in a patient's heart, comprising:

a DC-to-DC converter;

a pair of output switches coupled between an output of said DC-to-DC converter and a pair of electrodes adopted to be in or near said patient's heart; and a controller for activating said DC-to-DC converter and closing said switches to couple said DC-to-DC converter to said patient's heart.

11. The fibrillator of claim 10 wherein said controller is adapted to couple said DC-to-DC converter to said patient's heart for a predetermined time of between 0.03 and 5 seconds.

12. The fibrillator of claim 10 and further including high voltage capacitor means coupled to said DC-to-DC converter in parallel with said output switches.

13. The fibrillator of claim 10 and further including means for regulating a voltage level of an output of said DC-to-DC converter.

14. An automatic fibrillator for inducing fibrillation in a patient's heart, comprising:

a battery;

a pair of output switches coupled between an output of said battery and a pair of electrodes adopted to be in or near said patient's heart; and a controller for closing said switches to couple said battery to said patient's heart for a predetermined period of time between 0.03 and 5 seconds.

15. An implantable pulse generator for inducing fibrillation in a patient's heart comprising:

pulse generation means including a DC-to-DC converter having an output;

means for activating said DC-to-DC converter; and means for coupling the output of said DC-to-DC converter to said patient's heart to deliver a fibrillation inducing stimulus.

16. The pulse generator of claim 15, said means for coupling including:

a high voltage output stage having a pair of high voltage output switches; and means for closing said pair of high voltage output switches to deliver said fibrillation inducing shock.

17. The pulse generator of claim 16 and further including:

high voltage capacitor means coupled in parallel with said output switches; and means for coupling the output of said DC-to-DC converter for a predetermined time prior to closing said output switches.

18. The pulse generator of claim 15, said means for coupling comprising a pacing output stage.

19. The pulse generator of claim 15 and further including means for disconnecting the output of said DC-to-DC converter from said patient's heart.

20. The pulse generator of claim 19 wherein said means for disconnecting comprises means for opening said high voltage output switches.

21. The pulse generator of claim 15 and further including means for deactivating said DC-to-DC converter following a predetermined time period.

22. The pulse generator of claim 15 and further including means for sensing an electrogram signal from said patient's heart and means for delivering said fibrillation inducing shock to said patient's heart synchronous with a sensed R wave.

23. The pulse generator of claim 15 and further including means for receiving a command from an external control device to initiate delivery of said fibrillation inducing shock.

24. A method of inducing fibrillation in a patient's heart using an implantable pulse generator, comprising:

coupling a battery in said implantable pulse generator to electrodes in or near said patient's heart to deliver a fibrillation inducing stimulus; and following a predetermined time between 0.03 and 5 seconds, disconnecting said battery from said electrodes.

* * * * *